(12) United States Patent
Rashtchian (10) Patent No.: US 8,124,340 B2
(45) Date of Patent: Feb. 28, 2012

(54) METHODS FOR ENRICHMENT OF SELECTED RNA MOLECULES

(75) Inventor: Ayoub Rashtchian, Gaithersburg, MD (US)

(73) Assignee: Quanta Biosciences, Gaithersburg, MD (US)

( * ) Notice: Subject to any disclaimer, the term of this patent is extended or adjusted under 35 U.S.C. 154(b) by 7 days.

(21) Appl. No.: 12/692,592

(22) Filed: Jan. 23, 2010

(65) Prior Publication Data

US 2010/0297709 A1    Nov. 25, 2010

Related U.S. Application Data

(63) Continuation of application No. PCT/US2010/021897, filed on Jan. 22, 2010.

(60) Provisional application No. 61/146,647, filed on Jan. 22, 2009.

(51) Int. Cl.
*C12Q 1/68* (2006.01)
(52) U.S. Cl. ........................................ 435/6.1; 435/6.11
(58) Field of Classification Search .................. None
See application file for complete search history.

(56) References Cited

U.S. PATENT DOCUMENTS 6,518,026 B2 *  2/2003  Hartley ........................ 435/6.12
2003/0228620 A1 * 12/2003  Du Breuil Lastrucci ......... 435/6

* cited by examiner

*Primary Examiner* — Young J Kim
(74) *Attorney, Agent, or Firm* — Perkins Coie LLP (57) ABSTRACT

Improved methods of studying RNA molecules are provided. In particular, methods of treating mixtures of RNA molecules so as to enrich the mixture for a desired type of RNA molecule are provided. For example, the methods permit depletion of mRNA from complex mixtures to facilitate study of microRNAs in the mixture.

26 Claims, 2 Drawing Sheets

SEQUENCE LISTING

<160> NUMBER OF SEQ ID NOS: 4

<210> SEQ ID NO 1
<211> LENGTH: 17
<212> TYPE: RNA
<213> ORGANISM: Artificial Sequence
<220> FEATURE:
<223> OTHER INFORMATION: RNA oligomer,completely synthesized

```
<400> SEQUENCE: 1
ggauggcgga gcggucu                                                      17

<210> SEQ ID NO 2
<211> LENGTH: 61
<212> TYPE: DNA
<213> ORGANISM: Artificial Sequence
<220> FEATURE:
<223> OTHER INFORMATION: NUCLEIC ACID OLIGOMER,completely synthesized

<400> SEQUENCE: 2
ggttaaccca gaatggcggt aagggtgtgg taggcgagtc atttttttttt ttttttttt       60 t                                                                      61

<210> SEQ ID NO 3
<211> LENGTH: 21
<212> TYPE: DNA
<213> ORGANISM: Artificial Sequence
<220> FEATURE:
<223> OTHER INFORMATION: NUCLEIC ACID OLIGOMER,completely synthesized

<400> SEQUENCE: 3
ggttaaccca gaatggcggt a                                                 21

<210> SEQ ID NO 4
<211> LENGTH: 17
<212> TYPE: DNA
<213> ORGANISM: Artificial Sequence
<220> FEATURE:
<223> OTHER INFORMATION: NUCLEIC ACID OLIGMER,completely synthesized

<400> SEQUENCE: 4
ggatggcgga gcggtct                                                      17
```

METHODS FOR ENRICHMENT OF SELECTED RNA MOLECULES

This application claims priority to provisional application 61/146,647, filed Jan. 22, 2009, and PCT/US10/21897, filed Jan. 22, 2010, the contents of which are hereby incorporated by reference in their entireties.

FIELD

The methods described below are in the fields of molecular and cellular biology. The methods permit enrichment of RNA molecules from, for example, complex mixtures of RNA molecules.

BACKGROUND

Within a given cell, tissue or organism, there exist many mRNA species, each encoding a separate and specific protein. This fact provides a powerful tool to investigators interested in studying genetic expression in a tissue or cell. mRNA molecules may be isolated and further manipulated by various techniques, thereby allowing the elucidation of the full functional genetic content of a cell, tissue or organism. The identity and levels of specific mRNAs present in a particular sample provides clues to the biology of the particular tissue or sample being studied. Therefore, the detection, analysis, transcription, and amplification of RNAs are important procedures in modern molecular biology.

In addition to mRNA, cells contain a variety of noncoding RNAs, including components of the machinery of gene expression, such as tRNAs and rRNAs and regulatory RNAs that influence the expression of other genes. Noncoding RNAs are diverse and a significant fraction of the genes of all organisms do not encode proteins. One class of small non-coding RNAs—the microRNAs or miRNAs—has recently been recognized to be quite numerous and phylogenetically extensive. MicroRNA genes produce tiny transcripts of about 22 nucleotides in length and function as antisense regulators of other RNAs.

A common approach to the study of abundance level or presence or absence of a particular RNA is the production of complementary DNA (cDNA). In this technique, the RNA molecules from an organism are isolated from an extract of the cells or tissues of the organism. From these purified RNA molecules, cDNA copies may be made using the enzyme reverse transcriptase (RT) or DNA polymerases having RT activity, which results in the production of single-stranded cDNA molecules. The term "reverse transcriptase" describes a class of polymerases characterized as RNA dependent DNA polymerases. All known reverse transcriptases require a primer to initiate synthesis of a first strand cDNA transcript from an RNA template.

One commonly used reverse transcriptase (RT) is Avian myoblastosis virus (AMV) reverse transcriptase (Verma, *Biochem. Biophys. Acta* 473:1 (1977); Berger et al., *Biochemistry* 22:2365 2372 (1983)). This enzyme has 5'-3' RNA directed DNA polymerase activity, 5'-3' DNA directed DNA polymerase activity, and RNase H activity. RNase H is a processive 5' and 3' ribonuclease specific for the RNA strand for RNA DNA hybrids (Perbal, *A Practical Guide to Molecular Cloning*, New York: Wiley & Sons (1984)). Errors in transcription cannot be corrected by reverse transcriptase because known viral reverse transcriptases lack the 3'-5' exonuclease activity necessary for proofreading (Saunders and Saunders, *Microbial Genetics Applied to Biotechnology*, London: Croom Helm (1987)). Another common reverse transcriptase is from Moloney murine leukemia virus (M-MLV). See, e.g., Gerard, *DNA* 5:271 279 (1986) and Kotewicz et al., *Gene* 35:249 258 (1985). M-MLV reverse transcriptase substantially lacking in RNase H activity has been described. See, e.g., U.S. Pat. No. 5,244,797.

A common technique uses first-strand cDNA as a template for amplification by the polymerase chain reaction, PCR. This method, often referred to as RNA PCR or reverse transcriptase PCR(RT-PCR), exploits the high sensitivity and specificity of the PCR process and is widely used for detection and quantification of RNA. Recently, the ability to measure the kinetics of a PCR reaction by on-line detection in combination with these RT-PCR techniques has enabled accurate and precise measurement of RNA sequences with high sensitivity. This has become possible by detecting the RT-PCR product through fluorescence monitoring and measurement of PCR product during the amplification process by fluorescent dual-labeled hybridization probe technologies, such as the "TaqMan" 5' fluorogenic nuclease assay described by Holland et al. (*Proc. Natl. Acad. Sci. U.S.A.* 88, 7276 (1991)), Gibson et al. (*Genome Res.* 6, 99 (1996)), and Heid et al. (*Genome Res.* 6, 986 (1996)); or "Molecular Beacons" (Tyagi et al. *Nature Biotechnology* 14, 303 (1996)). Nazarenko et al. (*Nucleic. Acids Res.* 25, 2516 (1997)) have described use of dual-labeled hairpin primers, as well as recent modifications utilizing primers labeled with only a single fluorophore (Nazarenko et al., 30, No. 9 e37 (2002)). Another method is the addition of double-strand DNA-specific fluorescent dyes to the reaction such as: ethidium bromide (Higuchi et al., *Biotechnology* (1992) and Higuchi et al., *Biotechnology* 11, 102610, 413 (1993)), YO-PRO-1 (Ishiguro et al., *Anal. Biochem.* 229, 207 (1995)), or SYBR Green I (Wittwer et al., *Biotechniques* 22, 130 (1997)). The concept of combining amplification with product analysis has become known as "real time" PCR, also referred to as quantitative PCR, or qPCR.

In qPCR using a double-strand specific fluorescent dye the fluorescent signal generated at each cycle of PCR is proportional to the amount of PCR product. A plot of fluorescence versus cycle number is used to describe the kinetics of amplification and a fluorescence threshold level is used to define a fractional cycle number related to initial template concentration. Specifically, the log of the initial template concentration is inversely proportional to the fractional cycle number (threshold cycle, or Ct), defined as the intersection of the fluorescence versus cycle number curve with the fluorescence threshold. Higher amounts of starting template results in PCR detection at a lower Ct value, whereas lower amounts require a greater number of PCR cycles to achieve an equivalent fluorescent threshold (Ct) and are detected at higher Ct values. Typically, the setting of this fluorescence threshold is defined as a level that represents a statistically significant increase over background fluorescent noise. Since this occurs at an early stage in the PCR process when critical substrates are not limiting, quantification of starting template occurs over a broad dynamic range with high accuracy, precision, and sensitivity. However, real-time PCR quantification of mRNA is still bounded by limitations of the process of reverse transcription.

The RT-PCR procedure, carried out as either an end-point or real-time assay, involves two separate molecular syntheses: (i) the synthesis of cDNA from an RNA template; and (ii) the replication of the newly synthesized cDNA through PCR amplification. In the so called "uncoupled" RT-PCR procedure (e.g., two step RT-PCR), reverse transcription is performed as an independent step using the optimal buffer condition for reverse transcriptase activity. Following cDNA synthesis, the reaction is diluted to decrease MgCl$_2$, and deoxyribonucleoside triphosphate (dNTP) concentrations to conditions optimal for Taq DNA Polymerase activity, and PCR is carried out according to standard conditions (see U.S. Pat. Nos. 4,683,195 and 4,683,202). By contrast, "coupled" RT PCR methods use a common or compromise buffer for reverse transcriptase and Taq DNA Polymerase activities. In one version, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of Mn$^{++}$ then PCR is carried out in the presence of Mg$^{++}$ after the removal of Mn$^{++}$ by a chelating agent. Finally, the "continuous" method (e.g., one step RT-PCR) integrates the three RT-PCR steps into a single continuous reaction that avoids the opening of the reaction tube for component or enzyme addition. Continuous RT-PCR has been described as a single enzyme system using the reverse transcriptase activity of thermostable Taq DNA Polymerase and Tth polymerase and as a two enzyme system using AMV RT and Taq DNA Polymerase wherein the initial 65° C. RNA denaturation step was omitted.

SUMMARY

Improved methods for synthesizing cDNA and for detection and/or quantification of RNA are provided. More specifically, the methods increase both the efficiency of cDNA synthesis and the sensitivity and accuracy of quantification of gene expression. The methods are useful in gene discovery, genomic research, diagnostics and identification of differentially expressed genes and identification of genes of importance to disease.

In one aspect, there is provided a method for selective enrichment of one or more RNA sequences in a complex sample comprising (a) reverse transcribing at least one RNA molecule to produce an RNA:cDNA hybrid molecule, using at least one reverse transcriptase and an exo-sample nucleotide that is incorporated into the cDNA; (b) incubating the resulting cDNA:RNA hybrid with Rnase H and an enzyme that specifically digests the cDNA sequence containing exo-sample nucleotide residues. The exo-sample nucleotide may be a substrate for an enzyme, for example, the exo-sample nucleotide used may be dUTP and the enzyme used for digestion of the cDNA is uracil-N-glycosylase. Other exo-sample nucleotide residues may be, for example, bromodeoxyuridine, 7-methylguanine, 5,6-dihyro-5,6 dihydroxydeoxythymidine, or 3-methyldeoxadenosine.

In step (a) above, the primer used for reverse transcription may contain one or more exo-sample nucleotide residues, which may be the same or different. The reverse transcriptase may have Rnase H activity, and in this case no additional Rnase H need be added in step (b), although the skilled artisan will recognize that additional RNAse H optionally may be added. When the RT is Rnase H deficient or has reduced Rnase H activity such that the RNA strand of the hybrid is not degraded, then an RNAse H is added in step (b).

In some embodiments, more than one reverse transcriptase may be used in step (a).

In particular embodiments, the primer used for cDNA synthesis is oligo dU or oligo dT and the complex sample contains mRNA. The primer may also be a sequence-specific primer. The primer may be, for example, 6-12, 12-18, 18-25, 25-30, 30-40, or 40-100 bases long. An oligo dU or oligo dT may contain about 6-30 residues, for example. The oligo (dT) may be an anchored oligo(dT). In specific embodiments the 3' nucleotide of the anchored oligo(dT) may be dA, dC or dG, or the 3' end of the anchored oligo(dT) may be dAdA, dAdG, dAdC, dGdG, dGdA, dGdC, dCdC, dCdA, or dCdG. The oligo dT may contain at least one one exo sample nucleotide, for example a dU residue.

The RT may be a viral reverse transcriptase. Suitable RTs include, but are not limited to: AMV RT, RSV RT, MMLV RT, HIV RT, EIAV RT, RAV2 RT, TTH DNA polymerase, C. hydrogenoformans DNA polymerase, Sensiscript™, Omniscript™, SUPERSCRIPT I® RT, SUPERSCRIPT II® RT, SUPERSCRIPT III® RT THERMOSCRIPT® RT, and MMLV and Rnase H deficient mutants of these enzymes.

In any of the methods described above, any free exo-sample nucleotide remaining after step (a) may be degraded with a reagent that is suitable for selective degradation of the exo-sample nucleotide, such as an enzyme. For example, when the exo-sample nucleotide is dUTP, the dUTP remaining after step (a) may be degraded with dUTPase.

DETAILED DESCRIPTION

When RNA species are being analyzed, complexity of the sample and the total number of different RNA species present in the sample, can have profound effects on the sensitivity and accuracy of detection and/or quantification. This problem is especially true for RNA analytes that are present in low concentration and where the sample contains a significant amount of background RNA. This problem can be further exacerbated if there is any sequence homology between the analyte RNA and other RNAs present in the sample. This is a constant problem in dealing with detection and quantification of rarely expressed genes, regulatory RNAs such as microRNAs and detection of viral RNAs in complex biological specimens.

Although there are many RNA fractionation and purification methods and commercial products available for RNA purification, they generally require large amounts of starting material and are based on the physical characteristics of different RNAs rather than their sequence or type. For example, size fractionation has been used to attempt to purify microRNAs Methods for selective degradation of specific RNA species in a complex sample are provided. The methods are very flexible and can be modulated to deplete or effect removal of a few species of RNA based on their sequence or of an entire class of RNAs depending on the application of the method and the desired outcome.

The methods enzymatically form RNA:DNA hybrids from RNA molecules present in a mixture. One or more modified nucleotides are used in this first step that make the cDNA recognizable or degradable in a specific manner. RNAse H activity, which degrades RNA only in an RNA; DNA hybrid is used to degrade the RNA portion of the hybrid molecules. The methods therefore selectively remove unwanted RNA molecules from complex mixtures/samples and improves detection or accuracy of quantification for desired RNA analytes.

In one aspect, a complex RNA sample containing both poly A-tailed species and non poly-A molecules, can be treated using the methods described herein so that the poly-A containing RNA can be selectively digested and therefore removed as a potentially confounding species for further analyses. The resulting sample is therefore enriched for non-poly-A RNAs. In this case, reverse transcription uses a primer that hybridizes to the poly A tail of the RNA. Such cDNA synthesis using an "exo sample" nucleotide generates a cDNA that is recognizable based on the use of a particular "exo sample" nucleotide. In the meantime non-poly A RNA of the sample remains as single stranded RNA and is not converted into cDNA. cDNA synthesis using poly A RNA produces a RNA: DNA hybrid. These hybrids are substrates for RNAse H, which digests the RNA strand of these molecules. Moreover, since the cDNA strand was made using exo sample nucleotides it can also be digested specifically using an appropriate enzyme, making it impossible for the resulting product to be amplified.

Exo-Sample Nucleotides

Many different exo-sample nucleotides that can be incorporate into cDNA and that permit subsequence specific degradation reactions can be used and are available commercially and/or have been described in the literature. Alternatively, depending on the nature of the exo sample nucleotide used, the cDNA can be removed physically using an appropriate binding partner. For example, a biotin-containing nucleotide can be used and the cDNA removed using streptavidin. More generally, exo-sample nucleotides containing different antigenic moieties have been linked to nucleoside triphosphates and can be incorporated into DNA by DNA polymerases including reverse transcriptases. The cDNA molecule may then be selectively removed using an antibody or other binding molecule that recognizes the antigenic moiety. Examples of such nucleotides are Fluorescent moieties such as fluorescene, Texas Red, Cy3, Cy5 and many others that are commercially available from variety of sources (Invitrogen/Life Technologies, Carlsbad, Calif.; Amersham/GE Life Sciences; Sigma, St. Louis, Mo., and the like). Other moieties that have been used include antigenic moieties such as digoxigenin, biotin, and others (see Sigma and Roche Applied Sciences for commercial sources). It will be apparent to those skilled in the art that other non-natural or modified nucleotide can be used with the methods described herein.

"Exo-sample nucleotide", as used herein, refers to a nucleotide which is generally not found in a sequence of DNA. See U.S. Pat. No. 5,137,814. For most DNA samples, deoxyuridine is an example of an exo-sample nucleotide. Although the triphosphate form of deoxyuridine, dUTP, is present in living organisms as a metabolic intermediate, it is rarely incorporated into DNA. When dUTP is incorporated into DNA, the resulting deoxyuridine is promptly removed in vivo by normal processes, e.g. processes involving the enzyme uracil DNA glycosylase (UDG) (U.S. Pat. No. 4,873,192; Duncan, The Enzymes XIV: 565-586 (1981), both references herein incorporated by reference in their entirety). Thus, deoxyuridine occurs rarely or never in natural DNA. It is recognized that some organisms may naturally incorporate deoxyuridine into DNA. For nucleic acid samples of those organisms, deoxyuridine would not be considered an exo-sample nucleotide. Examples of other exo-sample nucleotides include bromodeoxyuridine, 7-methylguanine, 5,6-dihyro-5,6 dihydroxydeoxythymidine, 3-methyldeoxadenosine, etc. (see, Duncan, supra).

Other exo-sample nucleotides will be evident to those in the art. The presence of deoxyuridine, or any other exo-sample nucleotide, may be determined readily using methods well known to the art. Other exo-sample nucleotides may be envisioned. Numerous DNA glycosylases are known to the art. An exo-sample nucleotide which may be incorporated into DNA during DNA or cDNA synthesis and a DNA glycosylase that acts on it may be used in the methods described herein. For example, bromodeoxyuridine (BdUR) is well known in the art to be incorporated into DNA. DNA containing BdUR may be degraded on exposure to light under appropriate conditions.

The deoxyribonucleoside triphosphate dUTP exemplifies an exo-sample nucleotide which may be conveniently incorporated into an enzymatic cDNA synthesis and/or DNA amplification procedures, thereby resulting in deoxyuridine-containing DNA. The DNA products of such a reaction will normally contain many uracil bases. Treatment of DNA containing uracil bases with uracil DNA glycosylase (UDG) results in cleavage of the glycosidic bond between the deoxyribose of the DNA sugar-phosphate backbone and the uracil base. The loss of the uracil creates an apyrimidinic site in the DNA, which blocks DNA polymerase from using the DNA strand as a template for the synthesis of a complementary DNA strand. The presence of substantial numbers of apyrimidinic sites in each DNA target molecule interferes with amplification procedures which use DNA polymerase to synthesize copies of target DNA. It is also known that apyrimidinic sites are susceptible to breakage upon heating or exposure to basic pH.

The removal of uracil or other exo-sample nucleotides from DNA by action of DNA glycosylases results in DNA that contain abasic sites. This term has been used in the literature as a generic way of describing such nucleic acids molecules. Other methods may be used for degrading cDNA molecules or otherwise making them unsuitable for further enzymatic reactions such as PCR amplification or other methods of amplification and detection or quantification. It is known in the art that there are specific enzymes that cleave abasic sites and can be used as part of the methods described herein. These enzymes are part of the repair mechanism of practically all organisms and many such enzymes have been isolated and characterized. These enzymes are referred to as AP endonucleases (Apurinic/apyrimidinic endonuclease). There are four types of AP endonucleases that have been classified according to their sites of incision. Class I and class II AP endonucleases incise DNA at the phosphate groups 3' and 5" to the baseless site leaving 3'-OH and 5'-phosphate termini. Class III and class IV AP endonucleases also cleave DNA at the phosphate groups 3" and 5" to the baseless site, but they generate a 3'-phosphate and a 5'-OH Human AP Endonuclease (APE1), like most AP endoucleases, is of class II and requires an $Mg^{2+}$ in its active site in order to carry out its role in base excision repair.

"Uracil DNA glycosylase" (UDG), a term of art, refers to an enzyme which cleaves the glycosidic bond between the base uracil and the sugar deoxyribose, only when the monomeric nucleotide dUTP is incorporated into a DNA molecule, resulting in incorporation of a deoxyuridine moiety (Duncan (1981) in The Enzymes 14:565, ed.: Boyer P). The enzyme does not act upon free dUTP, free deoxyuridine, or RNA (Duncan, supra).

The use of exo-sample nucleotides to remove potential contaminants from PCR amplified samples has been described by Longo et al (Gene 93: 125-128 (1990), U.S. Pat. No. 5,035,996), herein incorporated by reference in their entireties. Longo describes the use of either dU-containing oligonucleotides or dUTP in the PCR-directed amplification of a target sequence.

Primers

For removal of mRNA that contains a polyA tail, oligo dT or oligo dU primers can be used for the cDNA synthesis step. For removal of other RNA molecules, sequence-specific primers can be used. The length of oligo dT or oligo dU or other primers to be used for cDNA synthesis can vary from 6 bases to 100 bases or even longer. Most primers generally used are in range of 10 to 40 bases long, although the skilled worker will recognize that any length may be used that permits the desired priming to occur. Other types of primers with different composition can be used in place of oligo dT. Examples of such compositions include, but are not limited to, oligo dT where the 3' base is A, or C, or G. Alternatively, two bases at the 3' end can be variable and can be any combination of A, C, or G. Other sequences or moieties that can base pair with poly A sequences of mRNA can also be used. An example, without limitation, is deoxyuridine, (dU). Other exo-sample nucleotides can be used in the primer sequence. The primer(s) used for cDNA synthesis can also contain ribonucleotide residues and be RNA primers or can contain both ribonucleotide and deoxyribonucleotide residues.

The primer used for cDNA synthesis can be any sequence depending on the purpose of the assays and can contain one or more exo-sample nucleotides.

The methods described above can be used for depletion or removal of mRNA species from a complex sample and therefore to provide effective enrichment of non-mRNA species in the sample. The non-mRNA species can be any RNA that does not contain a poly A tail. In a specific example, total RNA from a sample is mixed with a cDNA primer that contains dU residues, instead of dT, i.e. oligo dU. The oligo dU primer anneals to the polyA tail of the mRNA species present in a sample and a suitable reverse transcriptase is used for cDNA synthesis in the presence of dNTPs containing dUTP. The cDNA produced contains dU residues substituted for dT, and therefore is a substrate for the enzyme uracil-N-glycosylase or uracil DNA glycosylase. The resulting cDNA:mRNA hybrid is incubated with Rnase H to digest/remove the mRNA strands that are present in the RNA:DNA hybrids. The cDNA and the oligo dU primer in the reaction can be digested with UDG. These enzymatic degradation reactions can be sequential in any order, or simultaneous. This degradation process will specifically digest and deplete or remove mRNA species and the corresponding cDNA, while leaving intact the other RNA species that did anneal to the primer and make cDNA.

The resulting RNA in the sample is therefore enriched and less complex than the starting total RNA in the sample and can be used for a variety of analysis techniques, such as PCR amplification or hybridization. Many different amplification methods have been described in the past few years including, but not limited to, the ligase chain reaction, NASBA, LAT (Ligation Activated Transcription amplification); TAS (Transcription Activated Amplification) and numerous other methods. The method of enriching RNA molecules of interest prior to amplification or analysis can be used as part of any of these or other methods. Some of the above-mentioned amplification methods are isothermal while others require thermocycling, but both types may be used in conjunction with the methods described herein.

Reverse Transcriptases

Reverse transcriptases that may be used in the methods described herein include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase, Tne DNA polymerase (WO 96/10640 and WO 97/09451), Tma DNA polymerase (U.S. Pat. No. 5,374,553) and mutants, variants or derivatives thereof (see e.g., WO 97/09451 and WO 98/47912). Some RTs have reduced, substantially reduced or eliminated RNase H activity. An enzyme "substantially reduced in RNase H activity" as that term is used herein has less than about 20%, more preferably less than about 15%, 10% or 5%, and most preferably less than about 2%, of the RNase H activity of the corresponding wild type or RNase H+ enzyme such as wild type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz et al. *Nucl. Acids Res.* 16:265 (1988) and in Gerard et al. (1992) *FOCUS* 14:91. Other RTs that may be used include, but are not limited to, M-MLV H⁻ reverse transcriptase, RSV H⁻ reverse transcriptase, AMV H⁻ reverse transcriptase, RAV (rous-associated virus) H⁻ reverse transcriptase, MAV (myeloblastosis-associated virus) H⁻ reverse transcriptase and HIV H⁻ reverse transcriptase (see U.S. Pat. No. 5,244,797 and WO 98/47912).

Many types and mutants of reverse transcriptases are available commercially or have been described in the literature. Commercially available RTs include AMV RT, RSV RT, MMLV RT, HIV RT, EIAV RT, RAV2 RT, THERMOSCRIPT® RT, ASLV, Foamy Virus family of reverse transcriptases and Rnase mutants thereof, SUPERSCRIPT III® RT, SUPERSCRIPT II® RT, and SUPERSCRIPT® RT. Other examples include Sensiscript™ and OmniScript™ from Qiagen Corp. (Germantown, Md.)

Enzymes with lowered RNaseH activity or virtually no RNaseH activity are suitable for use in the methods described herein. Therefore, depending on the reverse transcriptase being used, additional RNAse H addition may or may not be necessary and all variations are within the scope of these methods. Rnase H is also a ubiquitous enzyme in many organisms and bacteria and is available from many sources. The most commonly used is RNASE H from *E. coli*, however, there are many sources for this type of enzyme (Schultz et al. *Virus Research*, 134(1-2): 86-103 (2008). Cerritelli et al. *FEBS J.* 276(6):1494-505 (2009); Tadokoro et al., *FEBS J.* 276(6):1482-93 (2009). Other enzymes and proteins with similar activity that may not be referred to as RnaseH also may be used.

Other suitable RTs include DNA polymerases and thermostable DNA polymerases having natural reverse transcriptase activity or that demonstrate RT activity under certain conditions. Examples are Tth DNA polymerase, DNA Polymerase I or Klenow fragment of DNA Polymerase I. All such enzymes are included without limitation in the scope of the present invention. Use of thermostable enzymes may present certain advantages in some situations, such as being able to control the stringency of annealing of primer or primers to RNA in the reverse transcription step. Under higher temperature the annealing and reaction may be more specific and advantageous for certain applications. Reaction conditions and specificity can be modified, as known in the art, by physical (temperature and/or time) or chemical means such as addition of compounds that affect the specificity of primer annealing and priming/extension. Many such compounds or additives are know in the art, glycerol, DMSO, Betain, Proline, being a small example. PCT/US99/05538 describes many compounds that affect the annealing and secondary structure of nucleic acids and may be used as part of the methods described herein.

Single Strand binding proteins (SSB) are known from a variety of organisms, including thermo-tolerant, thermophilic or psycrophilic organism, and can be used to improve specificity of primer annealing and extension during enzymatic reactions (see U.S. Pat. No. 5,605,824). US Application 20070059713 describes fusion proteins between polymerases and SSBs that can be used in the present methods. All such protein mixtures or fusions, including fusions to reverse transcriptases can be used in the present methods.

Depending on the specific requirements of the downstream processes for analysis of the RNA other modification or additions can be made to the methods of the invention. For example, one improvement would be to additionally treat the mixture with the enzyme dUTPase to remove the dUTPs in the mixture. This may be useful in subsequent cDNA synthesis and amplification of the analyte RNAs in the sample. Moreover, the resulting RNAs can be further purified using physical separation method to remove the low molecular weight digested DNA and RNA, and this may provide further advantages for some applications. If a different exo-sample nucleotide is used and there is a desire to remove or eliminate the extra nucleotides an appropriate enzyme or method would be necessary. Suitable exo-sample nucleotides and corresponding enzymes are known in the art and will be evident to those skilled in the art.

Uses of the Methods

The methods described herein are broadly applicable to a variety of RNA species and there is no limitation on the kind or sequence of the process used for cDNA synthesis. For example, one skilled on the art will appreciate that the methods described herein can be applied for enrichment of RNA sequences for detection of viral RNAs. Viral RNAs are generally not polyadenylated (i.e. retroviral sequences, HIV, SIV, etc). Detection of HIV is often carried out in very complex samples containing large quantity of cellular RNA. The presence of such large quantities of unrelated background sample RNA interferes with the sensitivity and accuracy of detection. The methods of invention described herein will improve detection of rare viral sequences.

As described above the sequence of the primer for cDNA synthesis can be any sequence. For example, the primer can be complementary to rRNA, and tRNA that represents the majority of cellular RNA species. Use of this method can provide an easy method for enrichment of mRNA species in a total RNA sample. It will become evident to those skilled on the art that a combination of primers containing dU residues can be used to deplete or digest a number of species of condensed RNA from complex samples.

The methods described herein also can be used to digest RNA species that are abundant. For example a number of housekeeping genes such as Actin and GAPDH are present in high concentration in the cellular RNA, and can be selectively removed using primers specific to the sequence in the methods of the invention. These primers can be combined with primers for rRNA and tRNA to enrich the desired RNA species of the sample. It will become evident to those skilled on the art that a wide range of variations and applications of the methods described herein are possible.

Although the foregoing refers to particular preferred embodiments, it will be understood that the methods described herein are not so limited. It will occur to those of ordinary skill in the art that various modifications may be made to the disclosed embodiments and that such modifications are intended to be within the scope of the present methods.

Example 1

This example demonstrates the difficulties of attempting to detect and quantify a microRNA in a complex sample of total cellular RNA. HeLa cell total RNA was used as a source of complex RNA containing many different RNA species, however, any RNA can be used. Since HeLa cells and other biologically derived RNAs contain various micro RNAs (miRNAs, or MIRS) and the exact quantity of each MIR is not known, we synthesized a microRNA mimic that normally does not exist in biological samples. The pure RNA was quantified accurately in its pure form and was used in conjunction with HeLa RNA or in pure form. This system provided a way to distinguish qPCR signal generated from specific amplification of the mimic RNA versus the non-specific signal generated from the complex HeLa RNA. The mimic RNA had the sequence 5' GGAUGGCGGAGCGGUCU 3' (SEQ ID NO: 1)

Enrichment protocol: For enrichment of desired RNA species (in this case micro RNAs and other RNAs without a poly A tail) complex samples were subjected to the following enzymatic enrichment protocol. Each 10 μL reaction contained:

2 μL of 5× cDNA synthesis buffer (qScript Flex cDNA kit, cat #95049 from Quanta BioSciences, Inc. Gaithersburg, Md. 20877).
0.4 μL dNTPs where TTP had been replaced with dUTP or a mixture of TTP and dUTP was used.
1 μL qScript RT (MMLV RT with normal RNAse H activity)
1 μL oligo dU 20 (2 μM final concentration)
5 μL sample RNA The reaction was mixed and incubated at 37° C. for cDNA synthesis for 15 minutes. Following cDNA synthesis samples were incubated with 1 unit of UDG (*E. coli* UDG) at 42° C. for 10 min. The control samples were incubated without addition of UDG. Following digestion of dU containing DNA with UDG the reactions were incubated at 95° C. for 5 min to inactivate the enzymes.

Analysis of microRNAs by qPCR: The following procedure was used for tailing of non polyA RNAs (including microRNAs) with Poly A Polymerase prior to conversion into cDNA which is subsequently amplified by qPCR. Each 15 uL reaction contained:

3 μL of 5× cDNA synthesis buffer
0.4 μL ATP (10 mM stock)
1-2 units of Poly A polymerase (Epicenter Biotechnologies or New England BioLabs)
11.5 μL RNA sample and water The reactions were mixed and incubated at 37° C. for 10 min followed by heating at 95° C. for 5 Min. After Poly A tailing reagents for cDNA synthesis were added as follows:

1 μL of 5× cDNA synthesis buffer
1 μL of AD1 dT adapter primer (10 μM stock)
0.5 μL of qScript reverse transcriptase
2.5 uL of water to bring the volume to 20 uL The sequence of AD1 dT adapter primer is:

(SEQ ID NO: 2)
5' GGTTAACCCAGAATGGCGGTAAGGGTGTGGTAGGCGAGTCA(T)$_{20}$ 3'

The reaction was mixed and incubated at 42° C. for 15 min for cDNA synthesis, followed by 95° C. for 5 min. Generally 2 μL of this reaction was used for qPCR using Perfecta SYBR green qPCR SuperMix (Quanta BioSciences, Gaithersburg, Md.). The primers for amplification were used according to the instructions of the SYBR green Supermix and had the sequences:

```
AD1:
5' GGTTAACCCAGAATGGCGGTA 3'    (SEQ ID NO: 3)

Smir-1:
5' GGATGGCGGAGCGGTCT 3'        (SEQ ID NO: 4)
```

Results: The above enrichment protocol was applied to HeLa RNA and was demonstrated to be useful in reduction or elimination of the non-specific products that arise from non specific amplification of sequences not related to microRNAs. We started with 100 ng of HeLa RNA in 2 duplicate samples. Two of the samples were treated with the enrichment protocol above prior to tailing with PolyA polymerase and cDNA synthesis, while the control samples were not treated with the enrichment protocol. When the resulting cDNAs were subjected to amplification with the Smir1 and AD1 primers, a significant amount of a non-specific amplification product with a melting temperature of 84° C. was observed from the control HeLa cDNA. When the cDNA from the enriched samples was analyzed, as expected, no amplification products were observed. As a positive control we also used the synthetic mimic as template for tailing and cDNA synthesis and observed the specific amplification product melting at 73° C. When the mimic RNA was added to HeLa RNA and was tested without enrichment, it produced 2 products melting at 73° C. and 84° C. which represented the specific and non-specific products, respectively. When the mimic RNA was added to HeLa RNA and was enriched, it only produced the specific product melting at 72° C.

Example 2

Enrichment protocol: For enrichment of desired RNA species (in this case micro RNAs and other RNAs without a poly A tail) complex samples were subjected to the following enzymatic enrichment protocol. Each 10 μL reaction contained:

2 μL of 5× cDNA synthesis buffer (qScript Select cDNA synthesis kit, cat # . . . from Quanta BioSciences, Inc. Gaithersburg, Md. 20877).
0.4 μL dNTp's where TTP had been replaced with dUTP (25 mM each dATP, dUTP, dGTP, dCTP).
1 μL qScript RT (MMLV RT with normal RNAse H activity)
1 μL oligo dT 20 (2 uM final concentration)
5 μL sample RNA The reaction was mixed and incubated at 37° C. for cDNA synthesis for 15 minutes. Following cDNA synthesis samples were incubated with 0.5 units of UDG (*E. coli* UDG) at 42° C. for 20 min. The control samples were incubated without addition of UDG. Following digestion of dU containing DNA with UDG the reactions were incubated at 95° C. for 5 min to inactivate the enzymes.

Analysis of microRNAs by qPCR: The following procedure was used for tailing of non polyA RNAs (including microRNAs) with Poly A Polymerase and conversion into cDNA which is subsequently amplified by qPCR. A 10 μL reaction mix was prepared as shown below and was added to 10 L RNA sample from enrichment step above, followed by incubation at 37° C. for 30 min. After tailing and cDNA synthesis, the reaction was heated to 95° C. for 5 min and then was diluted with addition of 80 μL TE buffer.

2 μL of 5× cDNA synthesis buffer
0.84 ATP (2.5 mM stock)
1 μL of AD1 dT adapter primer (10 μM stock)
1 uL dNTP (10 mM each dATP, dTTP, dGTP, dCTP)
1.8 units of Poly A polymerase (Epicenter Biotechnologies or New England BioLabs)
1.4 μl qScript RT (with Rnase inhibitor)
Water to bring the volume to 10 μL 5 μL of the diluted cDNA mix was used for qPCR using Perfecta SYBR green qPCR SuperMix (Quanta BioSciences). The primers used for amplification were AD1 and the Smir-1 according to the instructions of the SYBR Green Supermix.

Results: In this experiment 5 duplicate samples were prepared all of which had 100 ng of HeLa RNA and varying amounts of mimic RNA ranging from 0 to $10^5$, or $10^6$, or $10^7$ or $10^8$ copies. One set of these samples were enriched as described in protocol for example 2 while the other set served as control without addition of UDG. The results are shown in FIGS. 1-4.

Figure 1:
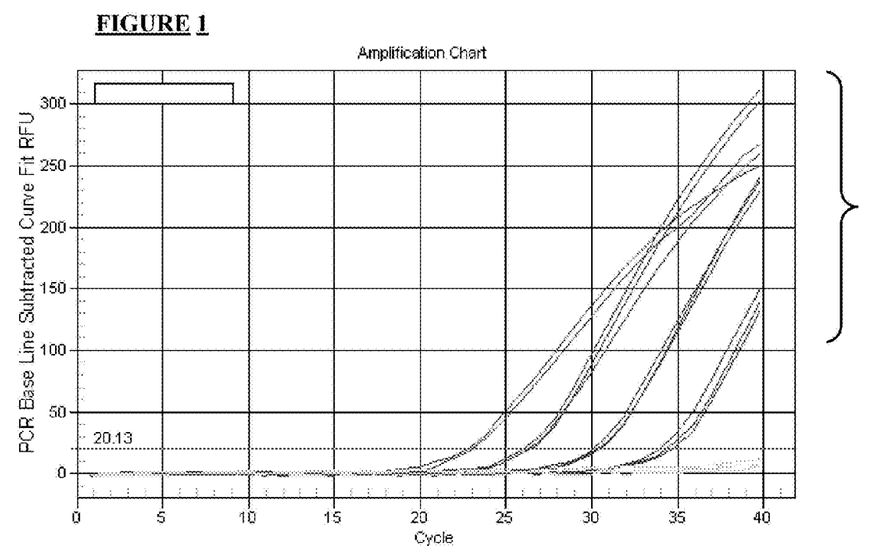
FIG. 1 shows a qPCR amplification profile of various reactions.
Figure 2:
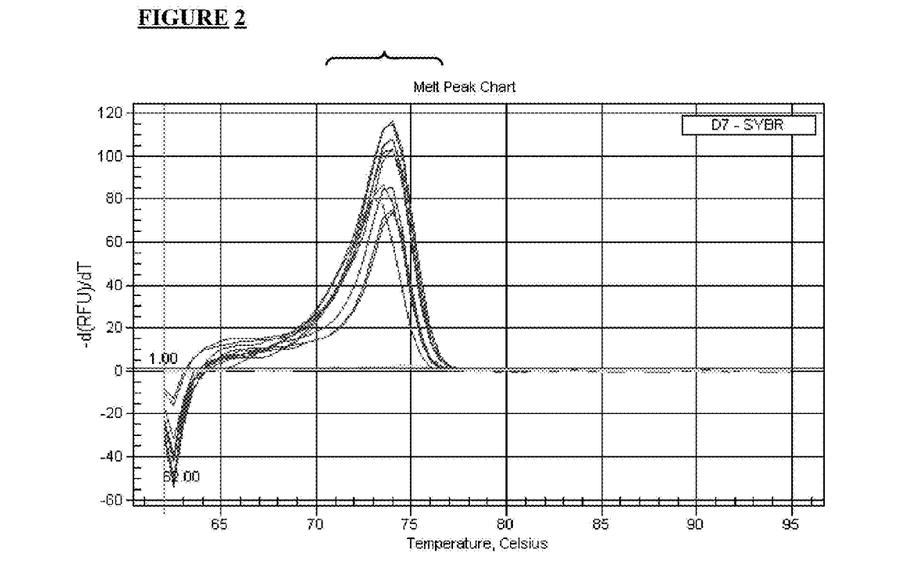
FIG. 2 shows the melting profile of the reactions in FIG. 1. A single amplification product (melting at 73 C, shown by brace) was observed from a sample containing a mimic RNA, while HeLa RNA without any mimic RNA (baseline) produced no amplification products.

FIG. 1 demonstrates the qPCR amplification profile and FIG. 2 shows the melting profile of the reactions in FIG. 1. As can be seen when the RNA was treated with UDG as in the enrichment protocol, a single amplification product (melting at 73 C, shown by brace) was observed from the sample containing mimic RNA, and the HeLa RNA without any mimic RNA (baseline) produced no amplification products.

Figure 3:
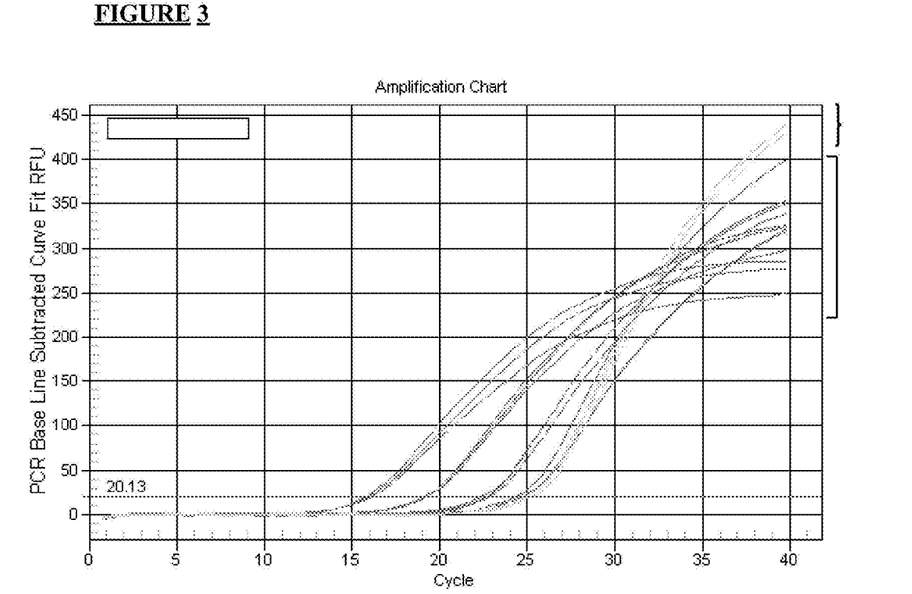
FIG. 3 shows a qPCR amplification profile.
Figure 4:
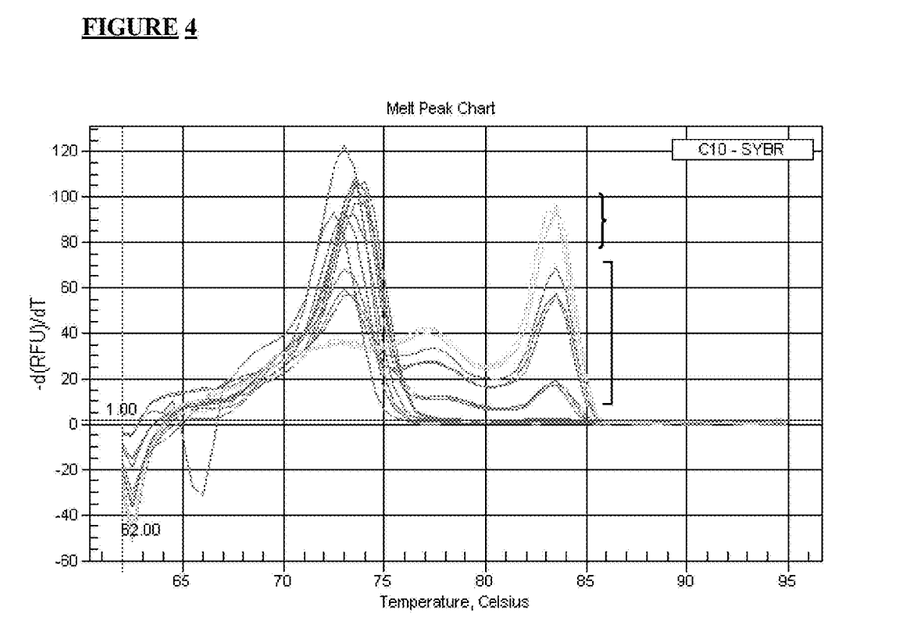
FIG. 4 shows the melting profiles of the reactions in FIG. 3. Three amplification products were observed from samples containing mimic RNA: specific product melting at 73 C; and 2 other non specific products melting at 77 C and 84 C (square brackets0. The HeLa RNA without any mimic RNA (curves shown by brace) produced the 2 non-specific amplification products melting at 77 C and 84 C.

FIG. 3 demonstrates the qPCR amplification profiles and FIG. 4 shows the melting profiles of the reactions in FIG. 3. As can be seen when the control RNA which was not treated with UDG as in the enrichment protocol, 3 amplification products were observed from sample containing mimic RNA: specific product melting at 73 C; and 2 other non specific products melting at 77 C and 84 C (square brackets0. The HeLa RNA without any mimic RNA (curves shown by brace) produced the 2 non-specific amplification products melting at 77 C and 84 C.

What is claimed is:

1. A method for selective enrichment of one or more RNA sequences in a complex sample comprising;
   a, reverse transcribing at least one RNA molecule to produce an RNA:cDNA hybrid molecule, using at least one reverse transcriptase and an exo-sample nucleotide that is incorporated into said cDNA;
   b, incubating the resulting cDNA:RNA hybrid with a source of Rnase H activity and an enzyme that specifically digests the cDNA sequence containing exo-sample nucleotide residues; thereby enriching one or more of said RNA sequences in the sample.

2. The method of claim 1, wherein said exo-sample nucleotide is a substrate for an enzyme.

3. The method of claim 1, wherein step (a) uses at least one primer comprising at least one exo-sample nucleotide.

4. The method of claim 1, wherein the Rnase H activity is provided by the reverse transcriptase, and no additional Rnase H is added.

5. The method of claim 1, wherein the RT is Rnase H deficient or has reduced Rnase H activity.

6. The method of claim 1, further comprising in step (b), adding Rnase H.

7. The method according, claim 1 where more than one reverse transcriptase is used in step (a).

8. The method according to, claim 1 wherein the exo-sample nucleotide used is dUTP and the enzyme used for digestion of cDNA is uracil-N-glycosylase.

9. The method according to claim 1 wherein the exo-sample nucleotide residues are chosen from the group consisting of: bromodeoxyuridine, 7-methylguanine, 5,6-dihyro-5,6 dihydroxydeoxythymidine, and 3-methyldeoxadenosine.

10. The method according to, claim 1 wherein a primer used for cDNA synthesis is oligo dU and said complex sample comprises mRNA.

11. The method according to, claim 1 wherein a primer used for cDNA synthesis contains an exo-sample nucleotide.

12. The method according to, claim 1 wherein more than 1 primer is used for cDNA synthesis.

13. The method according to claim 12, wherein the primers anneal to target abundant RNA species within the complex RNA mixture.

14. The method according to, claim 1 wherein said reverse transcription is carried out in the presence of oligo (dU) consisting essentially of between about 6 and about 30 residues.

15. The method according to, claim 1 wherein a primer for said cDNA synthesis is 6-12, 12-18, 18-25, 25-30, 30-40, or 40-100 bases long.

16. The method according to, claim 1 wherein said reverse transcription is carried out in the presence of oligo dT that is 6-12 or 12-18 or 18-25 or 25-30 or 30-40 or 40-100 bases long.

17. The method according to claim 1, wherein said at least one reverse transcriptase is a viral reverse transcriptase.

18. The method according to claim 1, wherein said reverse transcription is carried out in the presence of an anchored oligo(dT).

19. The method according to claim 18, wherein the 3' nucleotide of said anchored oligo(dT) is dA.

20. The method according to claim 18, wherein the 3' nucleotide of said anchored oligo(dT) is dC.

21. The method according to claim 18, wherein the 3' nucleotide of said anchored oligo(dT) is dG.

22. The method according to claim 18, wherein the 3' end of said anchored oligo(dT) is selected from the group consisting of dAdA, dAdG, dAdC, dGdG, dGdA, dGdC, dCdC, dCdA, and dCdG.

23. The method according to, claim 1 wherein said reverse transcription is carried out in the presence of an oligo(dT) which comprises at least one dU residue.

24. The method according to claim 23 wherein said oligo dT contains at least one exo sample nucleotide residue.

25. The method according to claim 1, further comprising degrading any free exo-sample nucleotide remaining after step (a) with an enzyme.

26. The method according to claim 25, wherein said exo-sample nucleotide is dUTP, and said dUTP is degraded with dUTPase.

* * * * *